United States Patent [19]

Rajamannan

[11] Patent Number: 5,707,938
[45] Date of Patent: Jan. 13, 1998

[54] METHOD AND PESTICIDE PRODUCT FOR KILLING SURFACE AND SUBSURFACE PESTS

[76] Inventor: A. H. J. Rajamannan, 2120 Argonne Dr., Mpls., Minn. 55421

[21] Appl. No.: 523,785

[22] Filed: Sep. 5, 1995

[51] Int. Cl.⁶ .......................... A01N 37/00; A01N 37/02; A01N 37/06
[52] U.S. Cl. .......................... 504/320; 504/157; 514/557; 514/558; 514/560
[58] Field of Search .................... 514/557, 558, 514/560; 504/320, 157

[56] References Cited

U.S. PATENT DOCUMENTS

| | | | |
|---|---|---|---|
| 4,073,887 | 2/1978 | McLean, Sr. | 424/147 |
| 4,678,116 | 7/1987 | Krishnakumar et al. | 236/25 A |
| 4,928,343 | 5/1990 | Kissinger | 15/209 D |
| 5,058,804 | 10/1991 | Yonekubo et al. | 236/12.12 |
| 5,234,117 | 8/1993 | Garvin | 215/11.4 |
| 5,366,995 | 11/1994 | Savage et al. | 514/558 |
| 5,398,247 | 3/1995 | Godrej et al. | 424/195.1 |

OTHER PUBLICATIONS

Prompt Abstract 93:516143 (1993); Abstracting HFD, Feb. 15, 1993, p. 110.

WPIDS Abstract 90-069378; Abstracting FR 2,634,103 (1990).

CABA Abstract 84:42505 (1983); Abstracting, Izvestiya Akademii Nauk. Kirgizskoi SSR, 1983, No. 2, pp. 37-39.

CABA Abstract 93:29501 (1992); Abstracting, Proceedings of the 3rd International Conference on Plant Protection in the Tropics, 1992, No. 6, pp. 161-167.

*Primary Examiner*—John Pak
*Attorney, Agent, or Firm*—Herman H. Bains

[57] ABSTRACT

A method and product for killing agricultural pests including insects, plants, plant rhyzomes, plant nuts, and fungi, comprises a toxic substance which includes fatty acids, soaps, and inorganic and organic acids. The pesticide toxin is heated to a temperature within the range of 100° F. to 215° F. The pesticide toxin is a low concentration within the range of 0.1% to 3% and, when applied to plants and the soil surface, rapidly kills pests. When the toxic concentration is injected into the soil, the toxic concentration volatilizes and the toxic vapors rapidly reach and kill insects, fungi, plant nuts and plant rhyzomes.

1 Claim, No Drawings

METHOD AND PESTICIDE PRODUCT FOR KILLING SURFACE AND SUBSURFACE PESTS

FIELD OF THE INVENTION

This invention relates to a pesticide product and method for killing weeds and insects at, above and below the soil surface.

BACKGROUND OF THE INVENTION

It is generally known that fatty acids of vegetable and animal origin, organic and inorganic acids including propionic, citric, acetic and lactic acids by themselves have abilities to denude leaves and plant tissue of the epidermis, and injure the external cuticular layer of insects and fungus. However, the concentrations of such acids needed to kill weeds, insects and fungi is quite high ranging from one to three percent. When these materials are used in high concentrations as a pesticide, this poses not only an economic problem (expense), but its use can also be hazardous to the user.

It is also pointed out that certain weeds have rhyzomes or nuts located in the soil, and certain harmful insects reside in the ground or in nests. It is difficult to kill such insects and weeds by simply spraying or applying the pesticide in the usual manner.

SUMMARY OF THE INVENTION

It is an object of this invention to provide a method and novel pesticide comprising an acid, a potassium soap or a sodium soap at low concentrations which when heated to a predetermined temperature and applied to above the ground surface or below the surface, will effectively kill plants, rhyzomes, nuts and insects and fungi.

DESCRIPTION OF THE PREFERRED EMBODIMENT

In the present invention, the pesticide comprising fatty acids of vegetable or animal origin, organic or inorganic acids and natural acids and other di and tri acids, are heated to a temperature of at least 100° F., and will kill plants, insects or fungi located above or below the soil. Soaps which are salts of fatty acids may include sodium or potassium soaps. For example, potassium stearate may be used as the fatty acid derivative. Natural acids include propionic, acetic, lactic, citric, malic and tartanic. Di and tri acids are also effective as the pesticide.

When the acids or soaps of acids are heated and applied to plants or below the soil surface, the volatile fatty acid will vaporize and thereby reach and kill insects, insect eggs, plant rhyzomes and plant nuts. This allows lower concentrations of the pesticide substance. In this regard, fire ants, termites and other harmful insects reside in the ground or in nests in buildings. When the heated volatile fatty acids vaporize, the noxious vapors will rapidly reach the insects, eggs and queen and quickly kill them.

Certain common weeds such as Cogan grass and nut sedge have rhyzomes or nuts located below the ground where energy is stored in these structures. While typical herbicides will kill the leaves of these weeds, the rhyzomes and nuts below the ground remain intact and unharmed and can emerge quickly with new leaves. When heated acids or soaps are injected into the ground, the fatty acids and soaps will volatize and attack the external cellular layer of the rhyzomes and nuts, and cause permanent injury leading to the death of the plant.

The fatty acids and soaps will be heated to a temperature of about 100° F. to 215° F. when applied as a pesticide. Weeds that are killed at a 3% concentration of fatty acids or soaps, and weeds that cannot be killed by acids or soaps at this or higher concentrations can be killed by raising the temperature of the acids or soaps, while requiring only low concentrations of the acids or soaps.

The concentrations will range from 0.1% to 3% depending on the particular plants, fungi and insects involved.

From the foregoing, it will be seen that I have provided a novel pesticide, and method of applying the same, comprising a fatty acid or soap, which when heated, effectively kills plant and insect pests while minimizing the danger to the user.

Thus it will be seen that I have provided a highly effective and safe pesticide which is believed to be more economical in use than any comparable pesticide.

What is claimed:

1. A method of killing agricultural pests including insects, plants, plant rhizomes, plant nuts, and fungi, comprises the steps of heating a low concentration solution of fatty acid or a soap wherein the concentration of soap or fatty acid is approximately within the range of 0.1 to 3%, by weight to a temperature within the range of 100° F. to 215° F. and then applying the solution to the surface of the ground and injecting the solution into the ground to kill surface and subsurface pests.

\* \* \* \* \*